(12) United States Patent
Niessner et al.

(10) Patent No.: US 6,271,327 B1
(45) Date of Patent: Aug. 7, 2001

(54) WATER-SOLUBLE POLYMERS AND THEIR USE IN COSMETIC FORMULATIONS

(75) Inventors: Manfred Niessner, Schifferstadt; Martin Rübenacker, Altrip; Claudia Nilz, Rödersheim-Gronau; Peter Hössel, Schifferstadt, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/230,352
(22) PCT Filed: Jul. 29, 1997
(86) PCT No.: PCT/EP97/04122
  § 371 Date: Jan. 25, 1999
  § 102(e) Date: Jan. 25, 1999
(87) PCT Pub. No.: WO98/04596
  PCT Pub. Date: Feb. 5, 1998

(30) Foreign Application Priority Data

Jul. 31, 1996 (DE) .............................. 196 30 977

(51) Int. Cl.$^7$ .............................. C08F 20/58; C08F 20/70; C08F 22/38
(52) U.S. Cl. .............................. 526/304; 526/303.1; 526/306; 526/307.1; 526/307.3; 526/310; 526/312; 424/70.1
(58) Field of Search .............................. 526/304, 303.1, 526/306, 307.1, 307.3, 310, 312

(56) References Cited

U.S. PATENT DOCUMENTS

| | | |
|---|---|---|
| 2,484,423 | 10/1949 | Reynolds . |
| 3,558,581 | 1/1971 | Beermann . |
| 4,275,002 | 6/1981 | Gless, Jr. . |
| 4,277,592 | 7/1981 | Eichhorn .............................. 526/227 |
| 4,403,072 | 9/1983 | Bunes .............................. 525/353 |
| 4,421,602 | 12/1983 | Brunnmueller et al. .............................. 162/168 |
| 4,478,553 | 10/1984 | Liebowitz et al. .............................. 416/97 |
| 4,713,236 | 12/1987 | Hoover et al. .............................. 424/70 |
| 4,722,958 | 2/1988 | Sauer et al. .............................. 524/379 |
| 5,001,198 | 3/1991 | Sekiya et al. .............................. 525/328 |
| 5,071,915 | 12/1991 | Sekiya et al. .............................. 525/123 |
| 5,430,110 | 7/1995 | Ahlers et al. .............................. 525/328 |
| 5,863,879 | 1/1999 | Zirnstein et al. .............................. 510/360 |

FOREIGN PATENT DOCUMENTS

| | | |
|---|---|---|
| 2040601 | 10/1991 | (CA) . |
| 1620977 | 3/1966 | (DE) . |
| 071050 | 2/1983 | (EP) . |
| 216387 | 4/1987 | (EP) . |
| 251182 | 1/1988 | (EP) . |
| 452758 | 4/1990 | (EP) . |
| 510246 | 10/1992 | (EP) . |
| 1082016 | 9/1967 | (GB) . |
| 3223304 | 11/1990 | (JP) . |
| 6122725 | 10/1992 | (JP) . |
| 07082320 | 9/1993 | (JP) . |
| 96/03969 | 2/1996 | (WO) . |

OTHER PUBLICATIONS

Fischer et al., *Macromol. Chem. Phys.*, 195, 679–687, 1994.
Emmerling et al., *Makromol. Chem.*, 184, 1441–1458, 1983.
Badesso et al., *Adv. Chem. Ser.*, 248, 1996, p490–504.

Primary Examiner—Fred Zitomer
(74) Attorney, Agent, or Firm—Keil & Weinkauf

(57) ABSTRACT

Water-soluble polymers whose characteristic structural elements comprise units of the formulae I and/or II

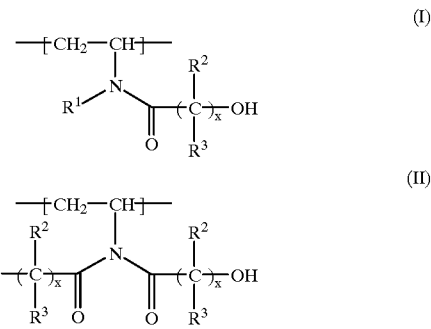

where $R^1$ is H, alkyl, cycloalkyl, aryl or aralkyl, $R^2$ and $R^3$ independently are as defined for $R^1$ or are selected from substituted alkyl, substituted cycloalkyl, substituted aryl or substituted aralkyl, the substituents being selected from OH, O-alkyl, O-aryl, SH, S-alkyl, S-aryl, $NH_2$, NH-alkyl, NH-aryl, $N(alkyl)_2$, possibly in protinated form, $N(Alkyl)_3{}^{+3}Z^-$, where Z is the radical of an inorganic or organic acid, COOH, COO-alkyl, $CONH_2$, CONH-alkyl, $CON(alkyl)_2$, CN and $SO_3H$; and the indices x are each independently an integer from 1 to 20; and the acid addition salts of these polymers, (processes for whose preparation are also described), are used in cosmetic compositions.

18 Claims, No Drawings

WATER-SOLUBLE POLYMERS AND THEIR USE IN COSMETIC FORMULATIONS

The invention relates to water-soluble polymers, to processes for their preparation and to their use in cosmetic compositions.

Polymers are widely employed in cosmetology and medicine. In soaps, creams and lotions, for example, they generally serve as formulation auxiliaries, for example as thickener, foam stabilizer or water-absorbent, or else to lessen the irritation caused by other ingredients or to improve the dermal application of active ingredients. Their function in hair cosmetology, in contrast, is to influence the properties of the hair. Thus conditioners are used in order to improve the dry and wet combing properties, feel, luster and appearance of the hair and to give it antistatic properties. Furthermore, they may have a setting effect, by forming hydrophobic films on the hair.

It is preferred to use water-soluble polymers having polar, frequently cationic functionalities, which have a greater affinity for the negatively charged surface of the hair. The structure and mode of action of various hair treatment polymers have been described in Cosmetics & Toiletries 103 (1988) 23. Examples of customary commercial conditioning polymers are cationic hydroxyethylcellulose, cationic polymers based on N-vinylpyrrolidone, acrylamide and diallyldimethylammonium chloride, or silicones.

U.S. Pat. No. 4,713,236 describes hair conditioners based on polymers containing vinylamine units. Mention is made therein in particular of polyvinylamine and its salts, α-substituted polyvinylamines, for example poly (α-aminoacrylic acid), or else copolymers containing, in addition to vinylamine, comonomers such as vinyl alcohol, acrylic acid, acrylamide, maleic anhydride, vinylsulfonate and 2-acrylamido-2-methylpropanesulfonic acid.

U.S. Pat. No. 5,478,553 discloses the use of homo- and copolymers of N-vinylformamide as hairsetting agents, especially in water-containing gels. Possible comonomers listed there are styrene, acrylic and methacrylic acid, and their esters and amides, vinyl esters and vinyl ethers. WO 96/03969, moreover, describes the use of such polymers as conditioners for shampoos.

JP 06 122 725 makes mention, inter alia, of the use of pulverulent N-vinylformamide homo- and copolymers in the cosmetics field.

Hydrolyzed oligomers of N-vinylformamide which can be employed as a constituent of body care compositions are known from U.S. Pat. No. 5,373,076.

EP 510 246 and Japanese Specification J0 3223-304 disclose crosslinked, predominantly anionic homo- and copolymers of N-vinylcarboxamides which are employed as water absorbers and thickeners in the cosmetics field. In addition, copolymers of acrylamide and methacrylic acid which may include N-vinylcarboxamides as well, as further monomers, are likewise employed as thickeners in DE 34 27 220.

EP 452 758 describes the use of water-soluble polymers containing, inter alia, N-vinylcarboxamide units as constituents of gels for dermal cosmetic and medical applications. According to DE 38 17 425, crosslinked hydrogels can also be used for this purpose.

The conditioner polymers known from the prior art, however, are still not entirely satisfactory. There is therefore a need for additional conditioner polymers having improved properties.

N-Vinylamide polymers with various structures are also known from other technical fields.

For example, polymers containing N-vinyl-N-alkylcarboxamide units are described in DE-A 28 29 652. Poly-N-vinyl-N-methylformamide is specified in U.S. Pat. No. 3,558,581, poly-N-vinyl-N-methylacetamide in GB 1 082 016.

Homopolymers of N-vinylformamide are known from U.S. Pat. No. 4,421,602 and EP-B-0 071 050. These polymers serve as a precursor for polymers containing copolymerized vinylamine units. For example, a description is given of copolymers containing from 90 to 10 mol-% of N-vinylformamide units and from 10 to 90 mol-% of vinylamine units. These polymers are obtained by free-radical polymerization of N-vinylformamide with subsequent hydrolytic cleavage of some of the formyl radicals using acids or bases. These polymers find application as auxiliaries in papermaking or as sludge flocculants.

EP 0 216 387 describes copolymers containing not only N-vinylformamide but also other ethylenically unsaturated monomers such as vinyl acetate, vinyl propionate, $C_1$- to $C_4$-alkyl vinyl ethers, esters, nitriles and amides of acrylic and methacrylic acid, and N-vinylpyrrolidone. Partial or complete hydrolysis of these copolymers likewise leads to copolymers containing copolymerized vinylamine units. EP 0 251 182 discloses copolymers which in addition to N-vinylformamide and vinylamine also contain acrylonitrile units, with or without small proportions of acrylamide units and acrylic acid units. These copolymers too find application in the paper industry.

The preparation of these known polymers is generally by free-radical homopolymerization or copolymerization of the corresponding monomers. owing to the poor availability of specifically substituted N-vinylcarboxamides, or their poor polymerizability, it is appropriate, by reaction of primary and secondary polymers containing vinylamine units with carboxylic acid derivatives, to obtain N-vinylcarboxamide functions. Macromol. Chem. Phys. 195 (1994) 679 describes the reaction of polyvinylamine with aliphatic carboxylic acid chlorides. The reaction with aromatic sulfonic acid chlorides to form the corresponding sulfonamides is known from U.S. Pat. No. 4,403,072 and U.S. Pat. No. 4,275,002. The formation of amide functions starting from polymers containing copolymerized vinylamine units, by reaction with carboxylic esters, on the other hand, is not described.

The reaction of polyvinylamine or its hydrochloride with various sugar lactones, for example glucolactone, is described in Macro-mol. Chem. 184 (1983) 1441. These reactions are generally carried out in nonaqueous polar solvents, requiring the complex isolation beforehand of polymers synthesized in aqueous solution.

Badesso et al. in Adv. Chem. Ser. 248 (1996) 490–504 describe preparing polyvinylamine by hydrolyzing poly(N-ethenylformamide). The preparation of certain polyvinylamid derivatives is also described. Described inter alia is a product of reacting polyvinylamine and γ-butyrolactone in which 24 mol % of the amine units are substituted by a radical of the formula

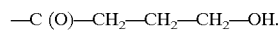

—C (O)—CH$_2$—CH$_2$—CH$_2$—OH.

The solvent used is methanol. Possible fields of use specified for the butyrolactone derivative are wastewater treatment and papermaking. A possibly advantageous possibility of employing the derivative in cosmetics is not mentioned.

It is an object of the present invention, therefore, to provide novel N-vinylamide polymers having improved cosmetic properties, and in particular to provide polymers which enhance the wet combing properties of head hair.

We have found that this object is achieved, surprisingly, by using polymers whose essential structural elements comprise hydroxy-substituted N-vinylcarboxamide units.

Unless specified otherwise, the following specific description of the invention is subject to the following definitions.

Alkyls that can be used in accordance with the invention comprise straight-chain or branched, saturated chains of 1 to 20 carbons, possible examples being alkyls of 1 to 12 carbons, such as the $C_1$–$C_6$-alkyls methyl, ethyl, n-propyl, i-propyl, n-butyl, sec-butyl, i-butyl, t-butyl, n-pentyl, sec-pentyl, i-pentyl, n-hexyl, 1-, 2- or 3-methylpentyl; and longer-chain radicals, such as unbranched heptyl, octyl, nonyl, decyl, undecyl, lauryl and the singly or multiply branched analogs thereof; and also alkyls with more than 12 carbons, such as unbranched tridecyl, myristyl, pentadecyl, palmityl, heptadecyl, stearyl, nonadecyl and eicosyl and the singly or multiply branched analogs thereof.

Cycloalkyls that can be used in accordance with the invention comprise, in particular, $C_3$–$C_{12}$-cycloalkyls, for example cyclopropyl, cyclobutyl, cyclopentyl, cyclohexyl, cycloheptyl, cyclooctyl, cyclopropylmethyl, cyclopropylethyl, cyclopropylpropyl, cyclobutylmethyl, cyclobutylethyl, cyclopentylethyl, cyclopentylpropyl, -butyl, -pentyl, -hexyl and the like.

Examples of aryls that can be used in accordance with the invention are phenyl and naphthyl, especially phenyl.

Examples of aralkyls that can be used in accordance with the invention are aryl-$C_1$–$C_{10}$-alkyls and especially aryl-$C_1$–$C_6$-alkyls, in which aryl and alkyl are as defined above.

The sum of all percentages (mol-%, % by weight) used in describing a composition is always 100.

The invention firstly provides polymers which are particuarly suitable for use in cosmetic compositions and whose essential structural elements comprise units of the formula I and/or II

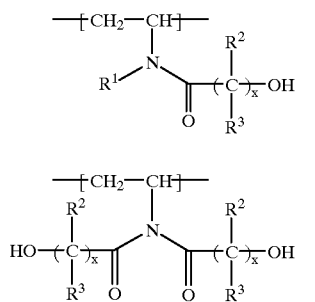

where
  $R^1$ is H, alkyl, preferably $C_1$–$C_{12}$-alkyl, cycloalkyl, preferably $C_3$–$C_{12}$-cycloalkyl, aryl, preferably phenyl, or aralkyl, preferably phenyl-$C_1$–$C_6$-alkyl,
  $R^2$ and $R^3$ independently are as defined for $R^1$, but alkyls are preferably $C_1$–$C_{20}$-alkyl, or are selected from the corresponding mono- or polysubstituted alkyls, cycloalkyls, aryls or aralkyls, the substituents being selected from OH, O-alkyl, O-aryl, SH, S-alkyl, S-aryl, $NH_2$, NH-alkyl, NH-aryl, N(alkyl)$_2$, possibly in protonated form, N(alkyl)$_3^+Z^-$, where Z is the radical of an inorganic or organic acid, COOH, COO-alkyl, $CONH_2$, CONH-alkyl, CON(alkyl)$_2$, CN and $SO_3H$; and
  the indices x are each independently an integer from 1 to 20, in particular 1 to 10, preferably 1 to 6;
and the corresponding acid addition salts of these polymers.

Polymers which are suitable for use in cosmetic compositions include those in which $R^2$ and $R^3$ independently are OH.

Preferred substituents of $R^2$ and $R^3$ are —OH, —O-$C_1$–$C_6$-alkyl, —O-phenyl, —SH, —S-$C_1$–$C_6$-alkyl, —S-phenyl, —$NH_2$, —NH-$C_1$–$C_6$-alkyl, —NH-phenyl, —N($C_1$–$C_6$-alkyl)$_2$, —N($C_1$–$C_6$-alkyl)$_3^+Z^-$, —COOH, —COO-$C_1$–$C_6$-alkyl, —$CONH_2$, —CONH-$C_1$–$C_6$-alkyl, —CON($C_1$–$C_6$-alkyl)$_2$, —CN and —$SO_3H$.

Preferred counterions $Z_-$ are $Cl^-$, $Br^-$, $H_2PO_4^-$, $SO_4^{2-}$, $NO_3^-$, $HCOO^-$, phenyl-$SO_3^-$.

A preferred embodiment of the invention provides novel polymers comprising
  a) from 0.1 to 100 mol-%, preferably from 25 to 100 mol-%, for example from 30 to 90, from 30 to 80, from 30 to 70 or from 30 to 60 mol-%, of units of the above formulae I and/or II,
  b) from 0 to 99.9 mol-%, preferably from 0 to 75 mol-%, for example from 10 to 70, from 20 to 70, from 30 to 70 or from 40 to 70 mol-%, of vinylamine units of the formula III

where $R^1$ is as defined above,
  c) from 0 to 99.9 mol-%, preferably from 0 to 60 mol-%, for example from 0 to 50, from 0 to 40 or from 20 to 40 mol-%, of monoethylenically unsaturated monomer units other than a) and b), preferably selected from N-vinylcarboxamides such as N-vinyl-$C_1$–$C_6$-carboxamides, N-vinylpyrrolidone, N-vinylcaprolactam, N-vinylurea, N-vinylimidazoles, N-vinylimidazolines, vinyl alcohol, vinyl formate, vinyl acetate, vinyl propionate, vinyl butyrate, $C_1$–$C_6$ vinyl ethers, monoethylenically unsaturated $C_3$–$C_8$ carboxylic and dicarboxylic acids and the esters, amides, anhydrides and nitrites thereof; and
  d) from 0 to 5 mol-%, for example from 0 to 3, from 0 to 2 or from 0 to 1 mol-%, of at least diethylenically unsaturated monomer units, preferably methylenebisacrylamide, glycol diacrylate, glycerol triacrylate, glycol dimethacrylate, glycerol trimethacrylate, divinylbenzene, divinyldioxane, pentaerythritol triallyl ether, pentaallylsucrose, divinylurea and divinylethyleneurea.

Particularly preference is given to using polymers comprising
  a) from 1 to 100 mol-%, in particular from about 5 to 100 mol-%, for example from 5 to 80, from 10 to 80, from 25 to 80, from 25 to 60, from 30 to 80 or from 30 to 60 mol-%, of units of the formula I and/or II where $R^1$ is H; $R^2$ and $R^3$ independently are selected from H, $C_1$–$C_6$-alkyl and phenyl; and x is an integer from 1 to 10,
  b) from 0 to 99 mol-%, in particular from about 0 to 95 mol-%, for example from 5 to 90, from 10 to 90, from 20 to 90, from 30 to 90 or from 30 to 80 mol-%, of vinylamine units of the formula III where $R^1$ is H, and
  c) from 0 to 99 mol-%, in particular from about 0 to 95 mol-%, for example from 0 to 60, from 0 to 50, from 0 to 40 or from 20 to 40 mol-%, of at least one other ethylenically unsaturated monomer selected from N-vinylformamide, N-vinylpyrrolidone, N-vinylcaprolactam, N-vinylurea, vinyl alcohol, vinyl formate, vinyl acetate, vinyl propionate, $C_1$–$C_6$ vinyl ethers, acrylic lacid, methacrylic acid and the esters, amides, anhydrides and nitriles thereof in cosmetic compositions.

Special preference is given to using polymers comprising a) from 1 to 100 mol-%, in particular from about 5 to 95 mol-%, for example from 5 to 80, from 10 to 80, from 25 to 80, from 25 to 60, from 30 to 80 or from 30 to 60 mol-%, of units of the formula I and/or II, where $R^1$ is H; one of $R^2$ and $R^3$ is H and the other is H or methyl; and x is an integer from 1 to 6; and b) from 0 to 99 mol-%, in particular from about 0 to 95 mol-%, for example from 5 to 90, from 10 to 90, from 20 to 90, from 30 to 90 or from 30 to 80 mol-%, of vinylamine units; and c) from 0 to 99 mol-%, in particular from about 0 to 95 mol-%, for example from 0 to 60, from 0 to 50, from 0 to 40 or from 20 to 40 mol-%, of N-vinylformamide units.

The present invention additionally provides a process for preparing polymers whose essential structural elements comprise units of the formula IV and/or V

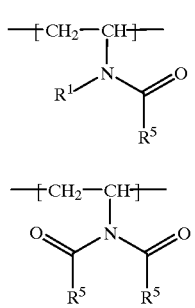

where $R^1$ is alkyl, cycloalkyl, aryl or aralkyl, and the radicals $R^5$ independently are selected from alkyl, cycloalkyl, aryl and aralkyl, unsubstituted or mono- or poly-substituted by OH, O-alkyl, O-aryl, SH, S-alkyl, S-aryl, $NH_2$, NH-alkyl, NH-aryl, $N(alkyl)_2$, possibly in protonated form, $N(alkyl)_3^{+Z-}$, where Z is the radical of an inorganic or organic acid, COOH, COO-alkyl, $CONH_2$, CONH-alkyl, CON$(alkyl)_2$, CN or $SO_3H$; or are a radical of the formula VI

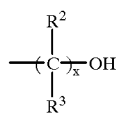

where $R^2$, $R^3$ and x are as defined above and $R^2$ and $R^3$ additionally and independently, can be OH, and the corresponding acid addition salts of such polymers, which comprises reacting a prepolymer comprising vinylamine units of the formula III

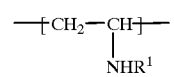

where $R^1$ is as defined above with a compound of the formula VII

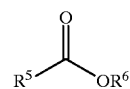

where $R^5$ is as defined above and $R^6$ is alkyl, aralkyl or aryl, or $R^5$ and $R^6$ together are a group of the formula VIa

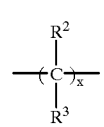

where $R^2$, $R^3$ and x are as defined above, and, if desired, converting the product to the corresponding acid addition salt.

In particular, a prepolymer is employed which comprises b) from 0.1 to 100 mol-% of vinylamine units of the formula III, c) from 0 to 99.9 mol-% of monoethylenically unsaturated monomer units other than a), and d) from 0 to 5 mol-% of at least diethylenically unsaturated monomer units.

Components b), c) and d) here are as defined above.

Using the novel process it is thus possible to prepare not only the novel polymers featuring the hydroxylated N-vinylcarboxamide units of the formulae I and II but also, in addition, all other polymers featuring units of the formulae IV and V.

In a first preferred variant of the novel process, polymers are prepared which feature units of the formulae I and/or II. To this end a prepolymer as defined above is reacted with lactones of the formula VIII,

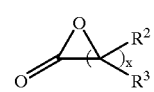

where $R^2$ and $R^3$ independently are H or OH or are $C_1$–$C_{20}$-alkyl, $C_3$–$C_{12}$-cycloalkyl, aryl or aralkyl which is unsubstituted or substituted by a functional group such as OH, O-alkyl, O-aryl, SH, S-alkyl, S-aryl, $NH_2$, NH-alkyl, NH-aryl, $N(alkyl)_2$ as free amine and/or in protonated form, $N(alkyl)_3^{+Z-}$, COOH, COO-Alkyl, $CONH_2$, CONH-alkyl, $CON(alkyl)_2$, CN or $SO_3H$; and x is an integer from 1 to 20.

Examples of suitable lactones are acetolactone (x=1), 2-methylacetolactone, 2,2-dimethylacetolactone, 2,2-diphenylacetolactone, 2-ethylacetolactone, 2,2-diethylacetolactone, 2-benzylacetolactone, β-propiolactone (x=2), 2-methyl-β-propiolactone, 3-methyl-β-propiolactone, 2,3-dimethyl-β-propiolactone, 3,3-dimethyl-β-propiolactone, 3-phenyl-β-propiolactone, 3-ethyl-β-propiolactone, 3-benzyl-β-propiolactone, γ-butyrolactone (x=3), 4-methyl-γ-butyrolactone, 3-methyl-γ-butyrolactone, 4-ethyl-γ-butyrolactone, 3,3-dimethyl-γ-butyrolactone, 4-phenyl-γ-butyrolactone, 4-benzyl-γ-butyrolactone, δ-valerolactone (x=4), γ-valerolactone, 2-methyl-δ-valerolactone, 5-phenyl-δ-valerolactone, 5-benzyl-δ-valerolactone, 2-ethyl-δ-valerolactone, 3-hydroxy-3-methyl-δ-valerolactone, ε-caprolactone (x=5) and Exaltolid (x=18) or else hydroxy-substituted lactones such as lactolactone or mandelolactone. Preferably, use is made of β-propiolactone, γ-butyrolactone, γ-valerolactone, δ-valerolactone and ε-caprolactone.

Also suitable are lactones of aldonic acids, for example glyceric acid, threonic acid, erythronic acid, ribonic acid, arabinic acid, xylonic acid, lyxonic acid, allonic acid, atronic acid, gluconic acid, mannonic acid, gulonic acid, idonic acid, galactonic acid and talonic acid, or aldonic acid lactones of di- and oligosaccharides such as maltose or cellobiose.

In accordance with a second preferred variant of the novel process, a prepolymer as defined above is reacted with carboxylic esters of the formula (VII)

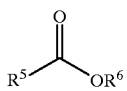

(VII)

where
R$^5$ is C$_1$–C$_{20}$-alkyl, C$_3$–C$_{12}$-cycloalkyl, aryl or aralkyl which is unsubstituted or substituted by a functional group selected from OH, O-alkyl, O-aryl, SH, S-alkyl, S-aryl, NH$_2$, NH-alkyl, NH-aryl, N(alkyl)$_2$ as free amine and/or in protonated form, N(alkyl)$_3{}^+$Z$^-$, COOH, COO-alkyl, CONH$_2$, CONH-alkyl, CON(alkyl)$_2$, CN and SO$_3$H; and R$^6$ is C$_1$–C$_6$-alkyl, aralkyl or aryl.

In the case of this process variant, the prepolymers preferably employed comprise, as copolymerized units
a) from 5 to 100 mol-% of primary vinylamine and
b) from 0 to 95 mol-% of other ethylenically unsaturated monomers from the group consisting of N-vinylformamide, N-vinylpyrrolidone, N-vinylcaprolactam, N-vinylurea, vinyl alcohol, vinyl formate, vinyl acetate, vinyl propionate, acrylic acid and/or acrylonitrile.

Examples of suitable esters of the formula VII which will be mentioned are methyl, ethyl, propyl, isopropyl, benzyl, phenyl, n-butyl, n-pentyl and n-hexyl esters of aliphatic and aromatic monocarboxylic acids, such as acetic, propionic, butyric, isobutyric, n-valeric, pivalic, capronic, cyclopentylcarboxylic, cyclohexylcarboxylic, enanthic, caprylic, nonanic, capric, lauric, myristic, palmitic, stearic, benzoic, 1-naphthalenecarboxylic, 2-naphthalenecarboxylic, phenylacetic and β-phenylpropionic acids or dicarboxylic acids, for example oxalic, malonic, succinic, glutaric, adipic, pimelic and suberic acids. These carboxylic acids can be unsubstituted or else substituted by functional groups such as OH, O-alkyl, O-aryl, halogen, SH, S-alkyl, S-aryl, NH$_2$, NH-alkyl, NH-aryl, N(alkyl)$_2$ as free amine and/or in protonated form, N(alkyl)$_3{}^+$Z$^-$, COOH, COO-alkyl, CONH$_2$, CONH-alkyl, CON(alkyl)$_2$, CN, SO$_3$H. Examples of substituted carboxylic acids are chloroacetic, bromoacetic, cyanoacetic, α-chloropropionic, β-chloropropionic, α-bromopropionic, β-bromopropionic, glycolic, lactic, maleic, tartaric, mandelic, salicylic, mercaptoacetic, α-mercaptopropionic and β-mercaptopropionic acids, glycine, N-methylglycine, N,N-dimethylglycine, choline, α-alanine, β-alanine, valine, leucine, isoleucine, serine, threonine, lysine, phenylalanine, thyrosine and proline. Also suitable are esters of polyhydric alcohols, for example glycol or polyglycols, glycerol, mannitol, sorbitol, glucose, in which case one or more hydroxyls can be esterified with carboxylic acids. Use is preferably made of acetic, propionic, butyric, benzoic, lauric, palmitic and stearic methyl esters or of triglycerides of higher fatty acids such as lauric, palmitic and stearic acid.

Reactions of carboxylic esters and lactones with amines are described in numerous literature references. Since the abovementioned prepolymers containing copolymerized vinylamine units are predominanently water-soluble, it is expedient to carry out the reaction with the esters or lactones of the formula VII or VIII, respectively, in the presence of water. Thus the reaction can be carried out both in aqueous solution and in mixtures of water with other inert solvents. Examples of suitable solvents are those in which the esters and lactones are soluble, such as methanol, ethanol, isopropanol, n-propanol, n-butanol, sec-butanol, tert-butanol, glycol, dimethylethylene glycol, tetrahydrofuran, dioxane, hexamethylphosphoramide, acetonitrile or acetone, and mixtures of these solvents. The reaction is preferably carried out in aqueous solution at a pH from 7 to 12, preferably from 9 to 11. It is also possible to conduct the reaction in a buffered solution, in which case the buffer system primary/secondary phosphate is particularly suitable. The concentration of the polymer in the aqueous solution, depending on molecular weight, is from 5 to 60% by weight, preferably from 10 to 30% by weight, such that the solution is readily stirrable during the reaction.

The reaction is carried out from 20 to 200° C., preferably from 40 to 120° C. and, with particular preference, at from 50 to 100° C. If the reaction is conducted at above the boiling point of the ester or lactone or of the inert solvent, it is performed under superatmospheric pressure in an appropriate pressure vessel. The reaction time is from 1 to 20 hours, preferably from 3 to 10 hours. The alcohols which are liberated when the amine functions are reacted with esters can, if desired, be removed by distillation in the course of the reaction and thus removed from the equilibrium.

Depending on the desired degree of amidation in the end product, from 1 to 5, preferably from 1 to 2.5, equivalents of ester or lactone are added for each vinylamine unit that is to be reacted. Secondary vinylamine units (R$^1$≈H) react exclusively to form structures of the formula I. In the case of primary amine functions, both the structures, I and II, are formed depending on the amount of lactone employed. Where the lactone is added in a substoichiometric amount, the formation of structure I is preferred.

The formation of amide decreases the number of basic groups and therefore the cationic charge density of the polymer, which can be detected by a polyelectrolyte titration. The degree of conversion with respect to the lactone employed is generally more than 50%, in the majority of cases more than 70%. After reaction is complete, the solution can be adjusted to the desired pH by adding acids or bases. However, another possibility is to isolate the polymer by precipitation in alcohols or acetone, or to free the solution by dialysis from low molecular mass components. The composition can be determined by elementary analysis and by $^1$H-NMR and IR spectroscopy.

In particular, the resulting polymers have molecular weights of from 1000 to 10 million, preferably from 10,000 to 5 million, corresponding to K values of from about 5 to 300 and from 10 to 250 respectively, measured on 1% strength aqueous solutions at a pH of 7 and 25° C. by the method of H. Fikentscher, Cellulose-Chemie, Volume 13, 58 to 64 and 71 to 74 (1932).

So as to obtain a substantially color-stable polymer solution in the course of storage, the reaction with the esters or lactones can be followed if desired by the addition of antioxidants, reducing agents or aldehyde scavengers. Antioxidants, which in most cases act as free-radical scavengers or UV stabilizers, are, for example, secondary aromatic amines, phenol, alkylphenols, thioethers, phosphites or mixtures of compounds from these classes of substance. Examples of suitable secondary aromatic amines are 4,4'-bis(phenylmethyl)diphenylamine, 4,4'-bis(tert-butyl) diphenylamine or mixtures thereof. Alkylphenols suitable as antioxidants are, for example, 2,6-dimethyl-4-tert-butylphenol, 2,4,6-trimethylphenol, 2,4-di-tert-butyl-6-methylphenol or mixtures thereof. Suitable thioethers are dialkyl 3,3'-thiodipropionate, poly-2,3-dimethylphenyl 1,4-disulfide, dibenzyl sulfide and dialkyl disulfides such as, for example, dioctadecyl disulfide.

Examples of suitable phosphite antioxidants are trisnonyl phenyl phosphite, di(2,4-di-tert-butylphenyl) pentaerythritol diphosphite and diphenylene decyl phosphite.

Examples of suitable reducing agents are sodium borohydride, sodium cyanoborohydride, dithionites, such as sodium, potassium or zinc dithionite, or hypophosphorous acid.

Examples of aldehyde scavengers are NH-containing compounds such as urea, ethyleneurea, melamine, guanidine, phenylguanidine or mixtures thereof. Mention may also be made of alkali metal bisulfites such as sodium or potassium bisulfite.

Antioxidants, reducing agents and aldehyde scavengers are each employed in amounts of from 0.01 to 20% by weight, preferably from 0.1 to 16% by weight, based on the polymers.

The prepolymers required as starting material for the implementation of the novel process are obtained by known methods, for example by free-radically initiated homo- and copolymerization of N-vinylcarboxamides of the formula IX,

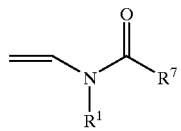

(IX)

where $R^1$ is as defined above and $R^7$ is H or $C_1$–$C_6$-alkyl followed by partial or complete, hydrolytic elimination of the group

preferably with the aid of acids, bases or enzymes.

The hydrolysis is preferably carried out in water under the action of acids, bases or enzymes, but can also be carried out in the absence of said hydrolyzing agents. Depending on the reaction conditions during hydrolysis, ie. the amount of acid or base, based on the polymer to be hydrolyzed and on the time and temperature of reaction, various degrees of hydrolysis result. Hydrolysis is continued to the point where from 0.1 to 100 mol-%, preferably from 1 to 99 mol-% and, with very particular preference, from 5 to 95 mol-% of the carboxylic acid residues have been hydrolytically eliminated.

Examples of acids suitable for the hydrolysis are mineral acids, such as hydrogen halide (in gaseous form or in aqueous solution), sulfuric, nitric or phosphoric acid (ortho-, meta- or polyphosphoric acid) or organic acids, for example $C_1$–$C_5$ carboxylic acids, such as formic, acetic or propionic acid, or aliphatic and aromatic sulfonic acids, such as methanesulfonic, benzenesulfonic and toluenesulfonic acid. In the case of hydrolysis with acids the pH is from 0 to 5. For each carboxylic acid residue in the polymer that is to be eliminated, from 0.05 to 1.5 equivalents of acid are required, preferably from 0.4 to 1.2.

In the case of hydrolysis with bases it is possible to use metal hydroxides of metals from main groups one and two of the Periodic Table of the Elements, examples being the hydroxides of lithium, sodium, potassium, calcium, strontium and barium. Also suitable, however, are ammonia or alkyl derivatives thereof, examples being alkyl- or arylamines such as triethylamine, monoethanolamine, diethanolamine, triethanolamine, morpholine, piperidine, pyrrolidine or aniline. With hydrolysis using bases, the pH is from 8 to 14. The bases can be employed in solid, liquid or possibly gaseous state and in dilute and undiluted form. Use is preferably made of ammonia, sodium hydroxide solution or potassium hydroxide solution. Hydrolysis in the acidic or alkaline pH range takes place at from 20 to 170° C., preferably from 50 to 120° C., and is over after from about 2 to 8 hours, preferably from 3 to 5 hours.

A procedure which has become particularly established is that in which the acids or bases are added in aqueous solution. Hydrolysis is generally followed by a neutralization such that the pH of the hydrolyzed polymer solution is from 3 to 12, preferably from 8 to 11. Neutralization is required when the continuing hydrolysis of partially hydrolyzed polymers is to be prevented or delayed.

Hydrolysis can also be undertaken with the aid of enzymes, for example amidases or proteases.

Hydrolysis may be accompanied by a further modification to the polymers, to the effect that the copolymerized comonomers are likewise hydrolyzed. Thus, for example, copolymerized vinyl ester units form vinyl alcohol units. Depending on the conditions of hydrolysis, the copolymerized vinyl esters may undergo complete or partial hydrolysis.

In the case of partial hydrolysis of copolymers containing vinyl acetate units, the hydrolyzed copolymer contains not only unchanged vinyl acetate units but also vinyl alcohol, N-vinylcarboxamide and vinylamine units. Units of monoethylenically unsaturated carboxylic anhydrides, carboxylic esters and carboxamides may give rise in the course of hydrolysis to carboxylic acid units. Copolymerized monoethylenically unsaturated carboxylic acids themselves are not altered in the course of hydrolysis. In addition, carboxamide and carboxylic acid units can be formed from copolymerized monoethylenically unsaturated nitriles. The degree of hydrolysis of the copolymerized comonomers can easily be determined by analysis.

The prepolymers obtained following hydrolytic cleavage have molecular weights of from 1000 to 10 million, preferably from 10,000 to 5 million, corresponding to K values of from about 5 to 300 and from 10 to 250 respectively, measured on 1% strength aqueous solutions at a pH of 7 and 25° C. by the method of H. Fikentscher, Cellulose-Chemie, Volume 13, 58 to 64 and 71 to 74 (1932).

Preference is given to prepolymers comprising units of
a) from 1 to 100 mol-% of primary vinylamine and
b) from 0 to 99 mol-% of other ethylenically unsaturated monomers from the group consisting of N-vinylformamide, N-vinylpyrrolidone, N-vinylcaprolactam, N-vinylurea, vinyl alcohol, vinyl formate, vinyl acetate, vinyl propionate, acrylic acid and/or acrylonitrile.

Particularly suitable prepolymers, for instance, are those consisting exclusively of vinylamine units of above formula III where the radicals $R^1$ can be identical or different and are H, $C_1$–$C_{12}$-alkyl, $C_3$–$C_{12}$-cycloalkyl, aryl or aralkyl. Preferred starting polymers are those with primary vinylamine units ($R^1$=H).

Further suitable prepolymers are copolymers comprising not only the vinylamine units but also up to 99.9 mol-%, preferably up to 95 mol-%, of other units of ethylenically unsaturated monomers. Examples which may be mentioned are N-vinylformamide, N-vinyl-N-methylformamide, N-vinyl-N-ethylformamide, N-vinylpropylformamide, N-vinyl-N-isopropylformamide, N-vinyl-N-butylformamide, N-vinyl-N-sec-butylformamide, N-vinyl-N-tert-butylformamide, N-vinyl-N-pentylformamide, vinyl alcohol, and vinyl esters of saturated carboxylic acids of 1 to 6 carbons, for example vinyl formate, acetate, propionate and butyrate. Also suitable are copolymers with unsaturated $C_3$–$C_8$ carboxylic acids, such as acrylic, methacrylic, maleic, crotonic, itaconic and vinylacetic acids, and the alkali metal and alkaline earth metal salts, esters, amides and nitrites thereof, examples being methyl acrylate, methyl methacrylate, ethyl acrylate, ethyl methacrylate, propyl acrylate and butyl acrylate, or with glycol and/or polyglycol esters of ethylenically unsaturated carboxylic acids, in each of which only one OH group of the glycols and polyglycols is esterified, examples being hydroxyethyl acrylate, hydroxyethyl methacrylate, hydroxypropyl acrylate, hydroxypropyl methacrylate, hydroxybutyl acrylate, hydroxybutyl methacrylate, or else with acrylic and methacrylic monoesters of polyalkylene glycols with a molar weight of from 1500 to 10,000.

Further suitable prepolymers are copolymers comprising esters of ethylenically unsaturated carboxylic acids with amino alcohols, for example dimethylaminoethyl acrylate and methacrylate, diethylaminoethyl acrylate and methacrylate, dimethylaminopropyl acrylate and methacrylate, diethylaminopropyl acrylate and methacrylate, dimethylaminobutyl acrylate and diethylaminobutyl acrylate. The basic acrylates are present here in the form of the free bases, of the salts of mineral acids, for example hydrochloric, sulfuric and nitric acid, of the salts of organic acids, such as formic or benzenesulfonic acid, or in quaternized form.

Examples of suitable quaternizing agents are dimethyl sulfate, diethyl sulfate, methyl chloride, ethyl chloride or benzyl chloride.

Further suitable prepolymers are copolymers containing copolymerized units of unsaturated amides, for example acrylamide, methacrylamide and N-alkylmono- and -diamides containing $C_1$–$C_6$-alkyls, for example N-methylacrylamide, N,N-dimethylacrylamide, N-methylmethacrylamide, N-ethylacrylamide, N-propylacrylamide and tertbutylacrylamide and also basic (meth)acrylamides, for example dimethylaminoethylacrylamide, dimethylaminoethylmethacrylamide, diethylaminoethylacrylamide, diethylaminoethylmethacrylamide, dimethylaminopropylacrylamide, dimethylaminopropylmethacrylamide, diethylaminopropylacrylamide and diethylaminopropylmethacrylamide.

Copolymers with units of $C_1$–$C_6$ vinyl ethers, for example vinyl methyl ether, vinyl ethyl ether, vinyl propyl ether, vinyl isopropyl ether, vinyl butyl ether, vinyl isobutyl ether, vinyl pentyl ether and vinyl hexyl ether, can also be used as prepolymers.

Additional suitable prepolymers are copolymers with units of N-vinylpyrrolidone, N-vinylcaprolactam, N-vinylurea and substituted N-vinylureas, for example N-vinyl-N'-methylurea, N-vinyl-N'-dimethylurea and N-vinylimidazole and substituted N-vinylimidazoles, such as N-vinyl-2-methylimidazole, N-vinyl-4-methylimidazole, N-vinyl-5-methylimidazole, N-vinyl-2-ethylimidazole and N-vinylimidazolines, for example N-vinylimidazoline, N-vinyl-2-methylimidazoline and N-vinyl-2-ethylimidazoline.

In this case the imidazole and imidazoline functions are in the form of the free bases or else in a form neutralized with mineral acids or organic acids, or else in quaternized form, quaternization preferably being performed with dimethyl or diethyl sulfate or with methyl or benzyl chloride.

Finally, other prepolymers which can be employed are copolymers containing monomer units having sulfo groups, examples being vinylsulfonic, allylsulfonic, methallylsulfonic or styrenesulfonic acid or 3-sulfopropyl acrylate, 3-sulfopropyl methacrylate and 2-acrylamido-2-methylpropanesulfonic acid. The compounds containing acid groups can be employed in the form of the free acids or of the ammonium, alkali metal or alkaline earth metal salts.

Further modifications in the prepolymers can be made by incorporating, by polymerization, from 0 to 5 mol-% of units of monomers having at least two ethylenically unsaturated, nonconjugated double bonds. Comonomers of this kind are commonly employed as crosslinkers in copolymerization reactions. The additional use of these comonomers during copolymerization brings about an increase in the molar masses of the copolymers. Examples of suitable such compounds are methylenebisacrylamide, esters of acrylic and methacrylic acid with polyhydric alcohols, for example glycol diacrylate, glycerol triacrylate, glycol dimethacrylate, glycerol trimethacrylate, and also polyols, such as pentaerythritol and glucose, that are esterified at least twice with acrylic or methacrylic acid. Other suitable crosslinkers are divinylbenzene, divinyldioxane, pentaerythritol triallyl ether, pentaallylsucrose, divinylurea and divinylethyleneurea.

The (co)polymerization for preparing the prepolymers can be carried out either in the presence or absence of an inert solvent or diluent. Since polymerization in the absence of inert solvents or diluents usually leads to nonuniform polymers, polymerization in an inert solvent or diluent is preferred. Suitable examples include those inert solvents in which the open-chain N-vinylcarboxamides are soluble. Inert solvents suitable for solution polymerization are, for example, those such as methanol, ethanol, isopropanol, n-propanol, n-butanol, tetrahydrofuran, dioxane, water and mixtures thereof. Polymerization can be carried out continuously or batchwise, and is performed in the presence of free-radical initiators which are employed in amounts of from 0.01 to 20% by weight, preferably from 0.05 to 10% by weight, based on the monomers. If desired, polymerization can also be initiated solely by the action of high-energy radiation, for example electron beams or UV rays.

To prepare polymers with low molecular weights, for example from 1000 to 100,000, preferably from 5000 to 50,000, polymerization is expediently conducted in the presence of regulators. Examples of suitable regulators are organic compounds containing sulfur in onded form. These include mercapto compounds, such as mercaptoethanol, mercaptopropanol, mercaptobutanol, mercaptoacetic acid, mercaptopropionic acid, butyl mercaptan and dodecyl mercaptan. Other suitable regulators are allyl compounds, such as allyl alcohol, aldehydes, such as formaldehyde, acetaldehyde, propionaldehyde, n-butyraldehyde and isobutyraldehyde, formic acid, ammonium formate, propionic acid, hydrazine sulfate and butenols.

If polymerization is conducted in the presence of regulators the amount of the latter required is from 0.05 to 20% by weight, based on the monomers employed in the course of the polymerization.

The monomers are normally polymerized in an inert gas atmosphere with the exclusion of atmospheric oxygen. During the polymerization, thorough mixing of the reactants is generally ensured. In the case of smaller batches, where safe dissipation of the heat of polymerization is guaranteed, the monomers can be polymerized batchwise by heating the reaction mixture to the polymerization temperature and then allowing the reaction to proceed. In this case polymerization is done in the range from 40 to 180° C. and it is possible to operate under superatmospheric pressure or else under reduced or elevated pressure. Polymers of high molecular weight are obtained if polymerization is carried out in water. This can be done, for example, to prepare water-soluble polymers in aqueous solution, as a water-in-oil emulsion, or by the technique of inverted suspension polymerization.

To prevent hydrolysis of the monomeric N-vinylcarboxamides during polymerization in aqueous solution, the polymerization is preferably carried out within a pH range from 4 to 9, in particular from 5 to 8. In many cases it is advisable, in addition, to operate in the presence of buffers as well, eg. primary or secondary sodium phosphate.

The novel polymers, especially those with monomer units of the formulae I and/or II, are employed as active substances in cosmetic preparations, for example as conditioners for shampoos, hair remedies, lotions, emulsions, rinses, gels, mousses and pretreatment and aftertreatment compositions for hair coloring and permanent waving, and also as hair setting agents and hairstyling compositions having haircare properties. In addition, they can be employed as thickeners in cosmetic formulations and in cosmetic preparations for oral care. It has surprisingly been found that the novel N-vinylcarboxamide copolymers have improved properties in cosmetic formulations. These improvements are most evident in shampoo formulations. The polymers are preferably used in customary commercial shampoo formulations containing sodium and/or ammonium lauryl ether sulfate as base surfactant with or without further co-surfactants such as alkylpolyglycosides, cocamidopropylbetaines, sulfosuccinic esters, secondary alkanesulfonates, α-olefinsulfonates, protein fatty acid condensates, N-acylsarcosinates, taurides, methyltaurides, fatty acid isethionates, N-acylglutamates, ethercarboxylic acid derivatives, alkylphosphate esters, alkylbetaines, alkylamidopropylbetaines, sulfobetaines, alkyl glyceryl ether sulfonates, cocosamphocarboxyglycinates and sorbitan derivatives. Using the novel polymers in the abovementioned shampoos brings about an improvement to, in particular, the wet-combability of the hair. In addition, the hair is given luster, volume and body as well as outstanding setting and antistatic properties.

The shampoos therefore have a washing, conditioning and setting action (3-in-1 shampoos), the polymers being effective even in small amounts. Good conditioning and setting effects are also shown by the copolymers containing N-vinylamine units in hair remedies, lotions, emulsions, rinses and styling compositions, such as gels and mousses, and in pretreatment and aftertreatment compositions for hair coloring and permanent waving, where they bring about outstanding care properties.

In addition, the copolymers can also be employed as conditioning agents and thickeners in skincare compositions, for example in creams, ointments, emulsions and lotions, and for oral care, for example in toothpastes, gels and mouthwashes.

In the cosmetic compositions, the novel polymers are normally present in a proportion of from about 0.01 to 15% by weight, for example from about 0.1 to 10% by weight, based on the overall weight of the composition. In addition to customary cosmetic vehicles it is possible for other common additives, such as surfactants, thickeners, gel formers, solubilizers, humectants, binders, propellants, polymers, for example silicones, sequestering agents, chelating agents, viscosity modifiers, clouding agents, stabilizers, pearlescence agents, colorants, fragrances, organic solvents, preservatives, pH regulators and, if desired, further conditioning agents to be present.

The invention will now be illustrated in more detail with reference to the following nonlimiting examples.

PREPARATION EXAMPLES

Examples 1 to 9 below describes the preparation of some novel polymers.

Example 1

500 g of an aqueous solution of polyvinylamine, polymer content 6.6% by weight ($\cong$767 mmol of vinylamine units), pH 10, K value 112 ($M_w \cong 300,000$), are charged to a stirred apparatus fitted with reflux condenser, thermometer and dropping funnel. 30 g ($\cong$348 mmol) of butyrolactone are added dropwise over the course of 10 minutes with vigorous stirring. The reaction mixture is subsequently heated at 80° C. for 3 h. After it has cooled to room temperature, the solution is adjusted to a pH of 7 using 7.5 g of concentrated formic acid. 537.5 g of copolymer solution are obtained with a viscosity of 13,440 mPas (Brookfield, 20° C.). The resulting polymer comprises 66.5 mol-% of vinylamine units and 33.5 mol-% of N-vinyl-γ-hydroxybutyramide units. Accordingly, 74% of the butyrolactone employed has reacted. The polymer content is 9.4% by weight.

Example 2

Reaction is as described in Example 1 with 500 g of polyvinylamine solution, polymer content 6.6% by weight ($\cong$767 mmol of vinylamine units), pH 10, K value 112 ($M_w \cong 300,000$), 19.8 g ($\cong$230 mmol) of butyrolactone and 4.6 g of formic acid. 524.4 g of copolymer solution are obtained having a polymer content of 8.6% and a Brookfield viscosity of 11,700 mPas (Brookfield, 20° C.). The degree of conversion (with respect to butyrolactone) is 72%. The copolymer is composed of 78.4 mol-% of vinylamine and 21.6 mol-% of N-vinyl-γ-hydroxybutyramide.

Example 3

Reaction is as described in Example 1 with 500 g of polyvinylamine solution, 38.0 g ($\cong$441 mmol) of butyrolactone and 0.7 g of formic acid. 538.7 g of copolymer solution are obtained with a polymer content of 12.9% and a Brookfield viscosity of 15,180 mPas. The degree of conversion (with respect to butyrolactone) is 83.6%. The copolymer is composed of 58.2 mol-% of vinylamine and 41.8 mol-% of N-vinyl-γ-hydroxybutyramide.

Example 4

500 g of an aqueous solution of a copolymer of 70 mol-% polyvinylamine and 30 mol-% N-vinylformamide, polymer content 7.7% by weight (≅524 mmol of vinylamine units), pH 10, K value 88 are charged to a stirred apparatus fitted with reflux condenser, thermometer and dropping funnel. 13.5 g (≅156.8 mmol) of butyrolactone are added dropwise over the course of 10 minutes with vigorous stirring. The reaction mixture is subsequently heated at 70° C. for 5 h. After it has cooled to room temperature, the solution is adjusted to a pH of 5 using 14 g of concentrated hydrochloric acid. 527.5 g of copolymer solution are obtained with a viscosity of 13,250 mPas (Brookfield, 20° C.). The resulting polymer comprises 56 mol-% of vinylamine units, 30 mol-% of N-vinylformamide units and 14 mol-% of N-vinyl-γ-hydroxybutyramide units. Accordingly, 67.3% of the butyrolactone employed has reacted. The polymer content is 9.0% by weight.

Example 5

Reaction is as described in Example 4 with 500 g of copolymer solution, 22.6 g (≅262 mmol) of butyrolactone and 8 g of hydrochloric acid. 530.6 g of copolymer solution are obtained with a polymer content of 10.2% by weight and a Brookfield viscosity of 16,105 mPas. The degree of conversion (with respect to butyrolactone) is 69.8%. The copolymer is composed of 46 mol-% of vinylamine units, 30 mol-% of N-vinylformamide units and 24 mol-% of N-vinyl-γ-hydroxybutyramide units.

Example 6

500 g of an aqueous solution of polyvinylamine, polymer content 22.6% by weight (≅2616 mmol of vinylamine units), pH 9, K value ($M_w$=≅10–20,000), are charged to a stirred apparatus fitted with reflux condenser, thermometer and dropping funnel. 89.4 g (≅783 mmol) of caprolactone are added dropwise over the course of 20 minutes with vigorous stirring. The reaction mixture is subsequently heated at 80° C. for 5 h. 589.4 g of copolymer solution are obtained. The resulting polymer is composed of 73.5 mol-% of vinylamine units and 26.5 mol-% of N-vinyl-6-hydroxycaproamide units. Accordingly, 88.4% of the caprolactone employed has reacted. The polymer content is 32.5% by weight.

Example 7

Reaction is as described in Example 6 with 500 g of copolymer solution and 149.3 g (≅1308 mmol) of caprolactone. 649.3 g of copolymer solution are obtained with a polymer content of 35.0% by weight. The degree of conversion (with respect to caprolactone) is 76.9%.

The copolymer is composed of 61.5 mol-% of vinylamine units and 38.5 mol-% of N-vinyl-6-hydroxycaproamide units.

Example 8

Reaction is as described in Example 6 with 500 g of copolymer solution and 209 g (≅1831 mmol) of caprolactone. 709 g of copolymer solution are obtained with a polymer content of 34.7% by weight. The degree of conversion (with respect to caprolactone) is 63.7%.

The copolymer is composed of 55.4 mol-% of vinylamine units and 44.6 mol-% of N-vinyl-6-hydroxycaproamide units.

Example 9

500 g of an aqueous solution of polyvinylamine, polymer content 25.2% by weight (≅2927 mmol of vinylamine units), pH 10, K value 30 ($M_w$=10–20,000) are charged to a stirred apparatus fitted with reflux condenser, thermometer and dropping funnel. 280 g (≅2057 mmol) of methyl benzoate are added dropwise over the course of 30 minutes with vigorous stirring. 300 g of N-methylpyrrolidone are added and the reaction mixture is heated at 90° C. for 8 h. After it has cooled to room temperature, the solution is adjusted to pH of 7 using 7.5 g of concentrated formic acid. 1087.5 g of copolymer solution are obtained. The resulting polymer is composed of 57.8 mol-% of vinylamine units and 42.2 mol-% of N-vinylbenzamide units. Accordingly, 60% of the methyl benzoate employed has reacted to form amide functions. The polymer content is 23.4% by weight.

USE EXAMPLES

Example 10

Conditioner Action of Novel Polymers

The novel polymers from Examples 1 and 2 (polymer 1 and 2 respectively) were compared with the known conditioner polymers 3 and 4 in respect of their conditioner action on head hair.

Polymer 1

Copolymer of 66.5 mol-% vinylamine and 33.5 mol-% N-vinyl-γ-hydroxybutyramide with a molecular weight of about 500,000.

Polymer 2

Copolymer of 78.4 mol-% vinylamine and 21.6 mol-% N-vinyl-γ-hydroxybutyramide with a molecular weight of about 500,000.

Polymer 3 (Comparison):

Commercial copolymer of acrylamide and diallyldimethylammonium chloride having an average molecular weight of about 1,000,000 (Merquat S from Merck Calgon).

Polymer 4 (Comparison):

Commercial cationic hydroxyethylcellulose (Celquat H 100 from National Starch).

For testing as conditioners for hair shampoos, the above-mentioned polymers 1 to 4 were added in the stated amount to a standard test shampoo containing 15.0% by weight of sodium lauryl ether sulfate having 2 to 3 ethylene oxide units (Texapon NSO from Henkel KG). On the basis of defined tresses of hair, the effect of the polymers was tested on the wet combing properties. For this purpose, the hair tresses were washed with the polymer-containing test shampoo and rinsed, and then the combing force was measured. The blank sample used was a tress of hair which had been treated with additive-free test shampoo. The results are given in Table 1.

The decreasing combing force is calculated by the following formula:

$$\text{Decrease } [\%] = \frac{\text{Measured value} \times 100}{\text{Blank value}} - 100$$

Accordingly, high decreases in combing force are evaluated as positive.

TABLE 1

| Polymer | Amount added (% by wt.) | Decrease in combing force (% rel. to blank value) |
|---|---|---|
| 1 | 0.1 | 38 |
| 2 | 0.1 | 30 |
| 3 (Comparison Example) | 1.0 | 18 |
| 4 (Comparison Example) | 0.1 | 25 |

We claim:

1. A polymer comprising units of formula I and/or II

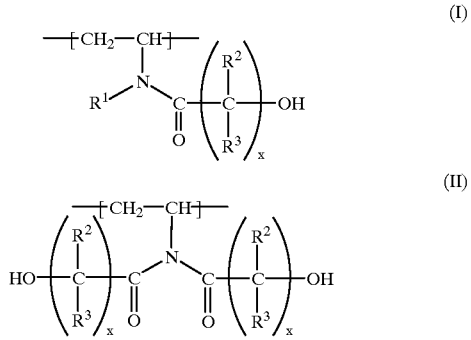

wherein each x is independently an integer from 1 to 20, $R^1$ is H, alkyl, cycloalkyl, aryl or aralkyl, and $R^2$ and $R^3$ independently are as defined for $R^1$ or are selected from substituted alkyl, substituted cycloalkyl, substituted aryl or substituted aralkyl, the substituents being selected from OH, O-alkyl, O-aryl, SH, S-alkyl, S-aryl, $NH_2$, NH-alkyl, NH-aryl, $N(alkyl)_2$, wherein the nitrogen atom is optionally in protonated form, $N(alkyl)_3^+Z^-$, where Z is the radical of an inorganic or organic acid, COOH, COO-alkyl, $CONH_2$, CONH-alkyl, $CON(alkyl)_2$, CN and $SO_3H$; or an acid addition salt of the polymer.

2. The polymer defined in claim 1, which has a weight-average molecular weight of from about $10^3$ to about $10^8$.

3. The polymer defined in claim 1, which comprises
   a) from 0.1 to 100 mol-% of units of the formula I and/or II,
   b) from 0 to 99.9 mol-% of vinylamine units of the formula III

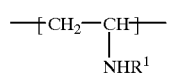

where $R^1$ is as defined above,
   c) from 0 to 99.9 mol-% of monoethylenically unsaturated monomer units other than a) and b); and
   d) from 0 to 5 mol-% of units of monomers having at least two ethylenically unsaturated double bonds.

4. A cosmetic composition comprising at least one Polymer as claimed in claim 1, in which $R^2$ and $R^3$, additionally and independently can be OH, in a cosmetic vehicle, alone or in combination with further cosmetically active substance.

5. The composition defined in claim 4 comprising an effective amount of said polymer as a thickener.

6. The composition defined in claim 4, which is selected from a hair cosmetic composition, a skin-care composition and an oral care composition.

7. The composition defined in claim 6, which is selected from a hairsetting composition, a hair remedy, a lotion, an emulsion, a rinse, a gel, a mousse, pretreatment and aftertreatment compositions for hair coloring and permanent waving, a hairstyling composition having care properties and a shampoo.

8. The shampoo composition defined in claim 7, comprising an amount of said polymer which is effective as conditioning agent.

9. The polymer defined in claim 1, which comprises from 1 to 100 mol-% of units of the formula I and/or II wherein $R^1$ is hydrogen, $R^2$ and $R^3$ are, independently of one another, selected from hydrogen, $C_1$–$C_6$-alkyl and phenyl, and the indices x are, independently from one another, an integer from 1 to 10.

10. The polymer defined in claim 3, which comprises from 25 to 100 mol-% of units of the formula I and/or II.

11. A process for the preparation of the polymer defined in claim 1, which comprises reacting a prepolymer comprising vinylamine units of formula III

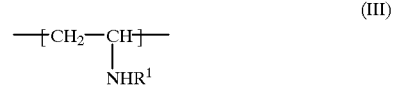

with a compound of formula VII

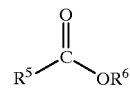

wherein $R^5$ is a radical of formula VI

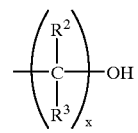

and $R^6$ is alkyl, aralkyl or aryl, or $R^5$ and $R^6$ together form a group of formula VIa

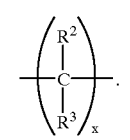

12. The process of claim 11, wherein $R^5$ and $R^6$ together form a group of formula VIa.

13. The process of claim 11, wherein the prepolymer comprises
   b) from 0.1 to 100 mol-% vinylamine units of the formula III,
   c) from 0 to 99.9 mol-% of monoethylenically unsaturated monomer units other than a) and b); and
   d) from 0 to 5 mol-% of units of monomers having at least two ethylenically unsaturated double bonds.

14. The process of claim 11, wherein the prepolymer is reacted in the presence of water.

15. A cosmetic composition comprising an amount of at least one polymer as defined in claim 1, which is effective for conditioning or thickening, in a cosmetic vehicle, alone or in combination with further cosmetically active substances.

16. The composition defined in claim 15, which is selected from a hairsetting composition, a hair remedy, a lotion, an emulsion, a rinse, a gel, a mousse, pretreatment and aftertreatment compositions for hair coloring and permanent waving, a hairstyling composition having care properties and a shampoo.

17. The polymer defined in claim 1, wherein the units of formula I and/or II are present in an amount of from 0.1 to 100 mol-%.

18. The composition defined in claim 4 comprising an effective amount of said polymer as a conditioning agent.

* * * * *